United States Patent
Hill et al.

(10) Patent No.: US 10,347,376 B2
(45) Date of Patent: Jul. 9, 2019

(54) SYSTEM AND METHOD FOR MODIFYING BIOMETRIC ACTIVITY USING VIRTUAL REALITY THERAPY

(71) Applicant: StoryUp, Inc., Columbia, MO (US)

(72) Inventors: Sarah E. Hill, Columbia, MO (US); Jeff M. Tarrant, Corvallis, OR (US)

(73) Assignee: StoryUp, Inc., Columbia, MN (US)

( * ) Notice: Subject to any disclaimer, the term of this patent is extended or adjusted under 35 U.S.C. 154(b) by 72 days.

(21) Appl. No.: 15/862,478

(22) Filed: Jan. 4, 2018

(65) Prior Publication Data
US 2018/0190376 A1     Jul. 5, 2018

Related U.S. Application Data

(60) Provisional application No. 62/442,330, filed on Jan. 4, 2017.

(51) Int. Cl.
*A61M 21/00*     (2006.01)
*G16H 20/70*     (2018.01)
(Continued)

(52) U.S. Cl.
CPC ............. *G16H 20/70* (2018.01); *A61B 5/048* (2013.01); *A61B 5/04012* (2013.01);
(Continued)

(58) Field of Classification Search
CPC .......... A61M 21/00; A61M 2021/0005; A61B 5/165; A61B 5/0482; G16H 20/70
(Continued)

(56) References Cited

U.S. PATENT DOCUMENTS 6,012,926 A    1/2000   Hodges et al.
6,057,846 A    5/2000   Sever, Jr.
(Continued)

FOREIGN PATENT DOCUMENTS

| CN | 106388793 A | 2/2017 |
|---|---|---|
| WO | 2016139576 A2 | 9/2016 |
| WO | 2016182974 A1 | 11/2016 |

OTHER PUBLICATIONS

International Search Report and Written Opinion for PCT/US2018/012421 dated Apr. 12, 2018.
(Continued)

*Primary Examiner* — John P Lacyk
(74) *Attorney, Agent, or Firm* — Husch Blackwell LLP

(57) ABSTRACT

Systems and methods for using virtual reality content as therapeutic treatment of psychological, psychiatric or medical conditions of a user are provided. The system may comprise a VR device for displaying the VR content to the user and one or more biometric monitors for monitoring the user's biometrics before, during and/or after exposure to the VR content. The system may further include a processor and one or more modules for analyzing the user's biometrics. The method may include the steps of measuring the user's initial biometric data, exposing the user to selected VR content, measuring the user's biometric data during and/or after exposure to the VR content, analyzing changes in the user's biometric data resulting from the selected VR content, determining whether the selected VR content as a positive effect on the psychological, psychiatric or medical condition of the user.

6 Claims, 10 Drawing Sheets
(5 of 10 Drawing Sheet(s) Filed in Color)

(51) Int. Cl.

| | | |
|---|---|---|
| *A61B 5/16* | (2006.01) | |
| *G06T 19/00* | (2011.01) | |
| *G06F 3/01* | (2006.01) | |
| *A61B 5/00* | (2006.01) | |
| *A61B 5/04* | (2006.01) | |
| *A61B 5/048* | (2006.01) | |
| *A61B 5/0482* | (2006.01) | |
| *A61B 5/021* | (2006.01) | |
| *A61B 5/024* | (2006.01) | |
| *A61B 5/08* | (2006.01) | |

(52) U.S. Cl.
CPC ............ *A61B 5/0482* (2013.01); *A61B 5/165* (2013.01); *A61B 5/74* (2013.01); *G06F 3/015* (2013.01); *G06T 19/003* (2013.01); *G06T 19/006* (2013.01); *A61B 5/021* (2013.01); *A61B 5/024* (2013.01); *A61B 5/0816* (2013.01); *A61B 5/486* (2013.01)

(58) Field of Classification Search
USPC ...................................................... 600/26–28
See application file for complete search history.

(56) References Cited

U.S. PATENT DOCUMENTS

| | | |
|---|---|---|
| 6,186,145 B1 | 2/2001 | Brown |
| 6,425,764 B1 | 7/2002 | Lamson |
| 9,179,855 B2 | 11/2015 | Burdea et al. |
| 9,406,096 B2 | 8/2016 | Bucolo et al. |
| 9,694,155 B2 | 7/2017 | Panova et al. |
| 9,712,736 B2 | 7/2017 | Kearns et al. |
| 2002/0128540 A1 | 9/2002 | Kim et al. |
| 2003/0135128 A1 | 7/2003 | Suffin et al. |
| 2005/0019734 A1 | 1/2005 | Peled |
| 2009/0287108 A1 | 11/2009 | Levy |
| 2011/0213197 A1 | 9/2011 | Robertson et al. |
| 2012/0036004 A1 | 2/2012 | Pradeep et al. |
| 2014/0058189 A1 | 2/2014 | Stubbeman |
| 2014/0276130 A1 | 9/2014 | Mirelman et al. |
| 2015/0079560 A1 | 3/2015 | Cowan |
| 2015/0306340 A1 | 10/2015 | Giap et al. |
| 2016/0077547 A1 | 3/2016 | Aimone et al. |
| 2016/0166219 A1 | 6/2016 | Majewski et al. |
| 2017/0228512 A1 | 8/2017 | Driscoll |
| 2017/0258389 A1 | 9/2017 | Howard |

OTHER PUBLICATIONS

Kovacevic et al., 'My Virtual Dream': Collective Neurofeedback in an Immersive Art Environment, PloS ONE 10.7, Public Library of Science, Jul. 8, 2015.

Bohil et al., Virtual Reality in Neuroscience Research and Therapy, Nature.com Dec. 2011 v. 12, Macmillan Publishers Limited.

Clemente et al., Contributions of Functional Magnetic Resonance in the Field of Psychological Treatments with Virtual Reality, Studies in Health Technology and Informatics pp. 197-201 v. 154, 2010.

Wiederhold et al., Virtual Reality with fMRI: A Breakthrough Cognitive Treatment Tool, Virtual Reality pp. 259-267 v. 12, 2008.

De Oliveira et al., Novel Virtual Environment for Alternative Treatment of Children with Cerebral Palsy, Computational Intelligence and Neuroscience v. 2016, May 23, 2016, Hindawi Publishing Publishing Corporation.

300 —

Stress Reduction and Pain Reduction:

Threshold Requirements:

- *EEG biometric data* – At least one z-score reduction of EEG Beta2 (25-35 hz) in the Cingulate Cortex region of brain AND/OR at least one z-score increase of EEG Alpha (8-12 hz) or EEG Alpha1 (8-10 hz) in the Cingulate Cortex region of the brain;
- *Heart Rate biometric data* – Significant increase in proportion of low frequency heart rate variability power to high and very low frequency;
- *Skin Temperature biometric data* – Significant increase in peripheral skin temperature;
- *Skin Conductance biometric data* – Significant reduction of skin conductance;
- *Blood Pressure biometric data* – Significant decrease in blood pressure;
- *Respiration biometric data* – Significant slowing of respiration OR Respiration that consistently matches a user's resonant breathing frequency OR Respiration that is stable at/around 6 breaths per minute.

304 —

Focus:

Threshold Requirements:

- *EEG biometric data* – At least one z-score increase of EEG Beta2 (25-35 hz) or EEG Gamma (35-50 hz) in the Anterior Cingulate region of the brain AND at least one z-score increase of EEG Alpha (8-12 hz) or EEG Alpha1 (8-10 hz) in the Posterior Cingulate region of the brain.

306 —

Quiet Mind:

Threshold Requirements:

- *EEG biometric data* – At least one z-score increase of Alpha (8-12 hz) or alpha1 (8-10 hz) in Precuneus region of the brain.

302 —

Mindfulness:

Threshold Requirements:

- *EEG biometric data* – At least one z-score increase of EEG Theta (4-8 hz) in the Anterior Cingulate Cortex region of the brain.

308 —

Open Heart:

Threshold Requirements:

- *EEG biometric data* – At least one z-score increase of EEG Gamma (35-50 hz) in the Anterior Cingulate region of the brain AND at least one z-score increase of EEG Gamma (35-50 hz) in the right Insula region of the brain OR
- *EEG biometric data* – At least one z-score increase of EEG Gamma (35-50 hz) in left frontal region of the brain AND at least one z-score increase of EEG Alpha (8-12 hz) in right frontal region of the brain.

Fig. 5

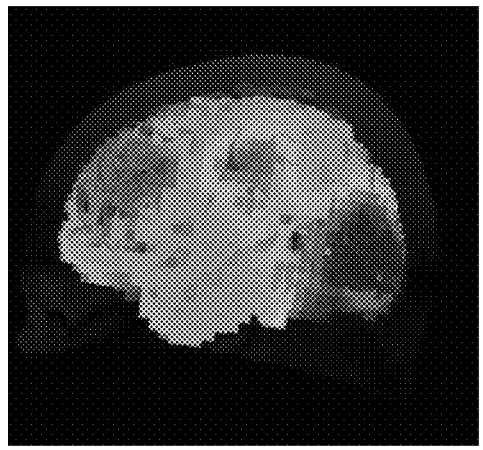 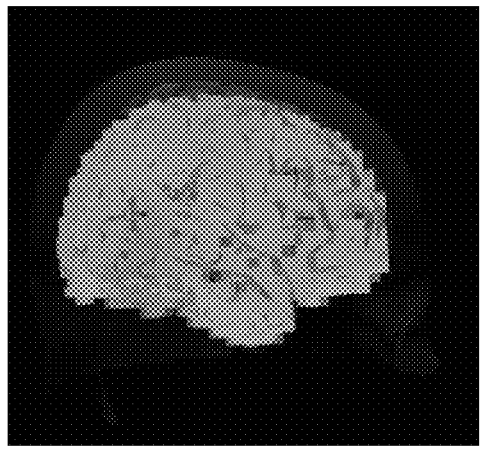
Fig. 8A
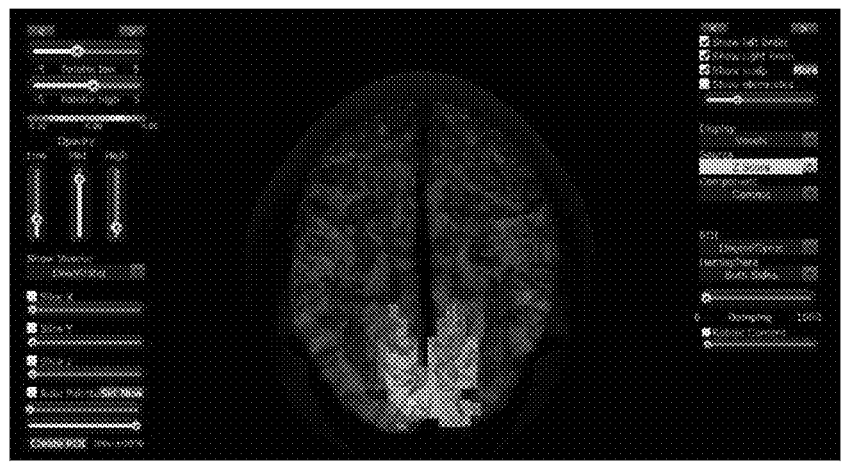
Fig. 8B

SYSTEM AND METHOD FOR MODIFYING BIOMETRIC ACTIVITY USING VIRTUAL REALITY THERAPY

CROSS-REFERENCE TO RELATED APPLICATIONS

This Application claims priority to U.S. Provisional Patent Application Ser. No. 62/442,330, filed on Jan. 4, 2017, to Sarah E. Hill and Jeffrey M. Tarrant, entitled "Method for Modifying Brainwave Activity Using Virtual Reality Therapy," the entire disclosure of which is incorporated herein by reference.

BACKGROUND OF THE INVENTION

The results of a National Institute of Mental Health (NIMH) sponsored survey indicate that 56 million American adults are affected by anxiety and depression. The combined economic impact of these disorders exceeds $250 billion dollars annually. These disorders are now commonly treated with a variety of medications and/or psychotherapeutic approaches. In the medication approaches, medications such as fluoxetine, which is commonly referred to by the trade name Prozac®, may be prescribed. In the psychotherapeutic approaches, therapies such as cognitive behavior therapy (CBT) may be employed. However, these medication and psychotherapeutic treatment approaches are not without shortcomings.

With medication approaches, in 20-30 percent of cases, prescriptions for the medications are never filled. In up to 50 percent of cases, the medications are not taken as prescribed. The reasons may include side effects, delayed therapeutic response, multiple doses per day, poor patient education, cost, access, and other various reasons.

With psychotherapy approaches, the shortcomings can include (1) the fact that the self-focus inherent in cognitive approaches may be beyond the abilities of some individuals and too intimidating or painful for others, (2) non-compliance with inter-sessional "cognitive homework," and (3) varying degrees of willingness to change or address problems.

Accordingly, a need exists for new approaches in treating psychological and psychiatric conditions, such as anxiety, depression, and phobias, as well as pain control.

SUMMARY OF THE INVENTION

The present invention is directed generally to systems and methods for using virtual reality ("VR"), augmented reality ("AR") and/or mixed reality ("MR") content in the therapeutic treatment of psychological, psychiatric or other medical conditions in patients. The present invention is also directed generally to systems and methods for providing specific VR and/or AR content to users as a therapeutic prescription to effect positive changes in the user's biometrics associated with emotional, psychological and/or psychiatric states.

According to one embodiment, the systems and methods of the present invention may be configured to provide new therapeutic methodologies implementing VR experiences, environments, and stories tailored to shift a user's brainwaves and other biometrics away from patterns associated with anxiety, depression and/or other psychological or psychiatric conditions and toward patterns associated with relaxation, positive affect, and pro-social emotional states. In such embodiments, the systems and methods can be configured to consistently provide shifts in a user's biometric data toward the desired biometric data pattern (such as EEG brainwave changes, blood pressure changes, heart rate changes, etc.) associated with positive changes in emotional or physical states of the user. For example, if a VR content experience is designed to create a relaxation response, the systems and methods of the present invention may be configured to provide biometric data shifts—such as EEG brainwave variations—that indicate a reduction of activation in brain regions associated with the stress response (e.g., cingulate cortex) as well as a subjective sense of reduced stress. On aspect is directed to a method for content categorization on the basis of percentage shifts in brain hertz.

According to one embodiment, the systems and methods of the present invention may be configured to analyze a user's EEG-type biometric data by analyzing the data as quantitative EEG (Qeeg) data using brainwave analysis software. The user's EEG-type biometric data may be measured during and/or after exposure to certain VR content and compared to previously measured EEG-type biometric data of the user to produce z-scores of change for specific brainwave types (i.e., alpha, delta, theta, etc.) in certain regions of the user's brain. The z-scores may then be used to identify statistically significant changes in the user's EEG-type biometric data (such as by identifying z-scores greater than or equal to 1.0).

According to one embodiment, the system of the present invention may include a VR headset, a VR content database module, a biometric reference database module, one or more biometric monitors and a processor configured with programming for controlling the operation of the system. The system may be configured to provide selected VR content from the VR content database module to a user or patient through the VR headset. The system may further be configured to measure and record specific biometric data from the user before, during and/or after the selected VR content is provided to the user. The system may further be configured to analyze the recorded biometric data to determine changes in the user's biometric data corresponding to the selected VR content to determine whether the selected VR content provides a positive therapeutic effect on the user's emotional, psychological and/or psychiatric states.

The present invention is also directed to one or more methods for using VR content as therapeutic treatment for a user. According to one embodiment of the present invention, the method may include one or more of the following steps: (i) measuring and recording a user's initial biometrics prior to exposure to selected VR content; (ii) creating a baseline biometric dataset for the user corresponding to the user's initial biometric data; (iii) selecting a first VR content and providing the first VR content to the user to expose the user to a first VR environment and experience; (iv) measuring and recording the user's biometrics during and/or after exposure to the first VR content; (v) creating a first biometric dataset for the user corresponding to the user's biometric data resulting from exposure to the first VR content; and (vi) comparing the user's first biometric dataset with the user's baseline biometric dataset to determine whether the first VR content had a positive therapeutic effect on the user.

The method of the present invention may further be configured to identify changes in the user's biometric data corresponding to the exposure of the first VR content and determine whether the identified changes in biometric data exceed one or more defined threshold requirements. The method of the present invention may further be configured to continue providing the first VR content if the defined threshold requirements are exceeded and configured to modify the first VR content and provide the modified VR content to the user if the defined threshold requirements are not exceeded.

Other aspects and advantages of the present invention will be apparent from the following detailed description of the preferred embodiments of the accompanying drawing figures.

DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee.

In the accompanying drawing, which forms a part of the specification and is to be read in conjunction therewith in which like reference numerals are used to indicate like or similar parts in the various views:

FIG. 5 is a schematic representation of virtual reality content profiles and biometric data threshold requirements for use in connection with the method of FIG. 4 in accordance with one embodiment of the present invention;

FIG. 8A is a brain image taken during a third case study;
FIG. 8B is a brain image taken during a third case study.

DETAILED DESCRIPTION OF THE INVENTION

Figure 1:
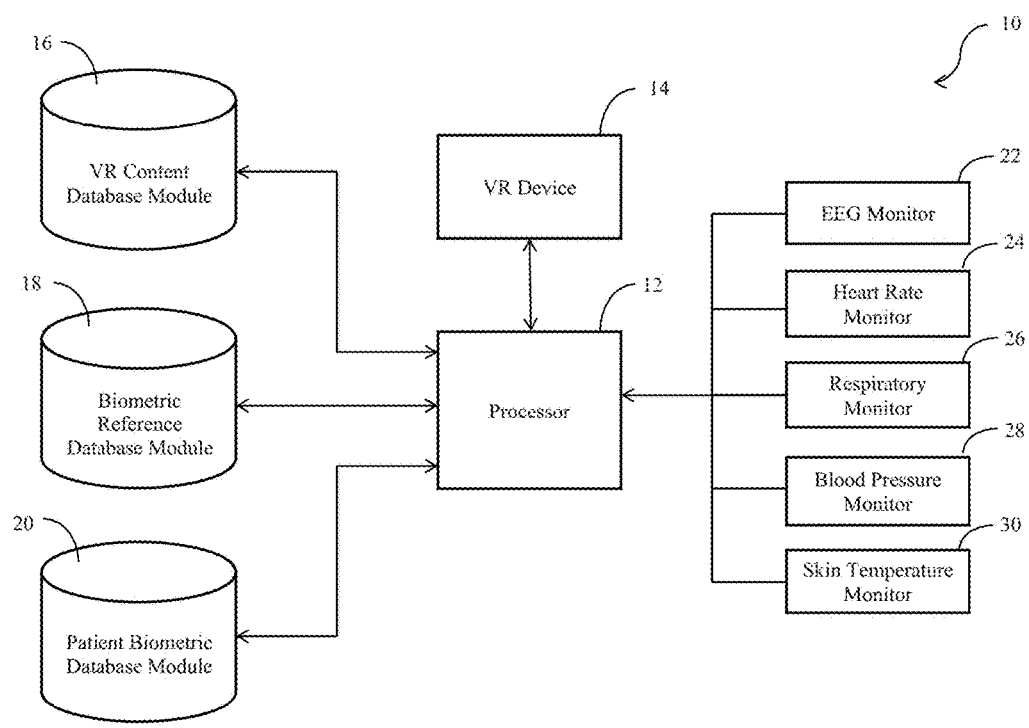
FIG. 1 is a schematic representation of a system for utilizing virtual reality content as therapeutic treatment of psychological, psychiatric or other medical conditions in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures. It will be appreciated that any dimensions included in the drawing figures are simply provided as examples and dimensions other than those provided therein are also within the scope of the invention.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

The present invention is directed generally to systems and methods for using virtual reality ("VR"), augmented reality ("AR") and/or mixed reality ("MR") content in the therapeutic treatment of psychological, psychiatric or other medical conditions in patients. The present invention is also directed generally to systems and methods for providing specific VR and/or AR content to users as a therapeutic prescription to effect positive changes in the user's biometrics associated with emotional, psychological and/or psychiatric states. The systems and methods of the present invention may be configured to provide VR, AR and/or MR experiences, environments and stories specifically tailored to shift specific biometrics of a user or patient away from patterns associated with anxiety, depression and/or other psychological or psychiatric conditions and toward patterns associated with relaxation, positive affect, and pro-social emotional states.

FIG. 1 shows a schematic illustration of a system 10 according to one embodiment configured to provide VR, AR and/or MR content to a patient or user and analyze the patient's or user's biometrics resulting from the provided VR, AR and/or MR content. System 10 may further be configured to be utilized in connection with one or more methods for using VR/AR/MR content in the therapeutic treatment of specified psychological, psychiatric or other medical conditions as described in greater detail below. The foregoing description of the present invention refers individually to the use of virtual reality (VR) components and concepts in connection with system 10 and methods 100 and 200 disclosed herein; however, it is recognized that augmented reality (AR) and mixed reality (MR) components and concepts may just as suitably be used in place of or in combination with VR components and concepts. As shown in FIG. 1, system 10 may include a processor 12, a VR device 14, a VR content database module 16, a biometric reference database module 18, and/or one or more biometric monitors 22-30 as schematically shown in FIG. 1. As also shown in FIG. 1, system 10 may also include a patient biometric database module 20 for storing biometric data of one or more patients or users of system 10 according to certain embodiments of the present invention.

Processor 12 can be any suitable type of computer processor configured for carrying out one or more sets of programming instructions and sending, receiving, processing and/or storing various types of data and information. According to one embodiment of the present invention, processor 12 may include an application program with programming instructions, that when executed by processor 12 cause the system 10 to carry out one or more steps and/or procedures for sending, receiving, processing and/or storing various types of data and information as described in greater detail below. Processor 12 can be configured to communicate with VR content database module 16 in order to access and transmit VR content based on determined parameters or instructions associated with a patient or user. Processor 12 can be configured to communicate with biometric reference database module 18 in order to access and utilize and biometric data and algorithms for analyzing and processing a patient's biometric data received by system 10. Processor 12 can also be configured to receive and process biometric data from monitors 22-30 and associated with a patient or user.

VR device 14 can be configured as any suitable type of virtual reality device, including but not limited to virtual reality devices commonly known in the art. According to one embodiment, VR device 14 can be configured as a headset that is worn over a user's eyes like a pair of goggles. The headset can block out external light and show a visual representation or image on one or more screens in front of the eyes. The view may be fully or partially immersive, providing a changing field of view in any direction the viewer chooses. VR device 14 can be coupled to a story, sound and/or music provided in association with selected VR content to augment the visual immersive experience of a user. The immersive media associated with the VR content can be monoscopic or stereoscopic 360-degree video or computer generated environments assessed with a variety of psychophysiological monitoring methods, including but not limited to, heart rate variability, muscle tension, skin conductance, and electroencephalogram (EEG).

VR content database module 16 can be configured as any suitable storage component and can store a plurality of different VR content accessible by processor 12. Depending on the particular embodiment, VR content database module 16 may comprise a reference library containing a plurality of categorized VR content that is tagged and organized based on content's effectiveness in treatment for certain emotional, psychological psychiatric and/or other medical conditions. Database module 16 may further be configured as a searchable database that may be queried by processor 12 to select a desired or appropriate VR content from the plurality of VR content stored in module 16.

Sensors or monitors 22-30 can be configured to monitor, record and/or collect certain types of biometric data of a patient or user before, during and after the user engages with selected VR content through system 10. According to one embodiment, system 10 includes an electroencephalogram (EEG) monitor 22 to monitor the EEG activity of a user. Brain computer interface (BCI) or EEG monitor 22 can be configured as an EEG headband or EEG electrocap that is placed on or around the head of the user of system 10. The EEG headband or cap can include a plurality of electrodes designed to measure brainwave activity. The EEG headband or cap can be attached via a wire ribbon to an FDA-approved amplifier that monitors and records the electrical activity of the user's brain. EEG monitor 22 may also be configured as a brain computer interface, such as but not limited to those developed by Muse, Emotiv and Neurable. Depending on the particular embodiment, EEG monitor 22 can be configured to monitor one or more brainwave frequencies, including but not limited to alpha, beta, delta, gamma, and theta, in one or more selected regions of the brain. At no point is electrical activity delivered to the user, as this monitor 22 is simply a recording technique. There is no risk to the user aside from possible mild discomfort from wearing the EEG headband or cap.

System 10 can additionally include a plurality of additional monitors for monitoring and recording additional biometric data of a user in connection with system 10, including but not limited to: a heart rate monitor 24 configured to monitor the heart rate variability of the user; a respiratory sensor 26 configured to monitor the breathing patterns of the user; a blood pressor monitor 28 configured to monitor the blood pressure of the user; and a skin conductance and temperature monitor 30 configured to monitor variations in the external temperature of the user.

System 10 can be used in connection with a user in order to provide VR content from VR content database module 16 and monitor the user's biometric data through monitors 22-30. System 10 can be utilized by fitting a user with VR device 14 and monitors 22-30. Processor 12 may be configured to communicate with VR content database module 16 to receive selected VR content and then transmit the selected VR content to VR device 14. Through VR device 14, the selected VR content can provide a VR environment and experience to the user. Before, during and/or after the selected VR content is provided to the user through VR device 14, processor 12 can be configured to monitor and record the user's biometrics via monitors 22-30 as biometric data. For reference, a user's biometrics as referred to herein can include, but are not limited to EEG readings (including one or more frequencies of brainwaves), heart rate, blood pressure, respiratory patterns, and skin temperature and conductance. Processor 12 may further be configured to analyze the recorded biometric data. As part of the analysis, processor 12 may be configured to transmit the data to biometric reference database 18 and/or query the database 18 for algorithms and procedures configured used to process the data to assess variations in the data influencing the psychological or psychiatric condition of the user as a result of the selected VR content provided to the user through VR device 14. According to one embodiment of the present invention, processor 12 may include an application program comprising programming instructions, that when executed by processor 12, cause the system to carry out the steps and procedures above.

In connection to system 10, the present invention is further directed toward a method 100 for treating a psychological, psychiatric or medical condition in a patient through selected VR content. Method 100 may be configured to provide targeted VR content to a patient that exposes the patient to a specific VR environment or experience aimed at enacting positive changes in emotion, consciousness and psychological and psychiatric states as measured through changes in specific biometric parameters of the patient. The method 100 may be further configured to analyze biometric data from the patient to determine whether the provided VR content has the desired effect on the patient as measured by the changes in the patient's biometrics, and/or provide different VR content where the desired effect is not achieved.

Figure 2:
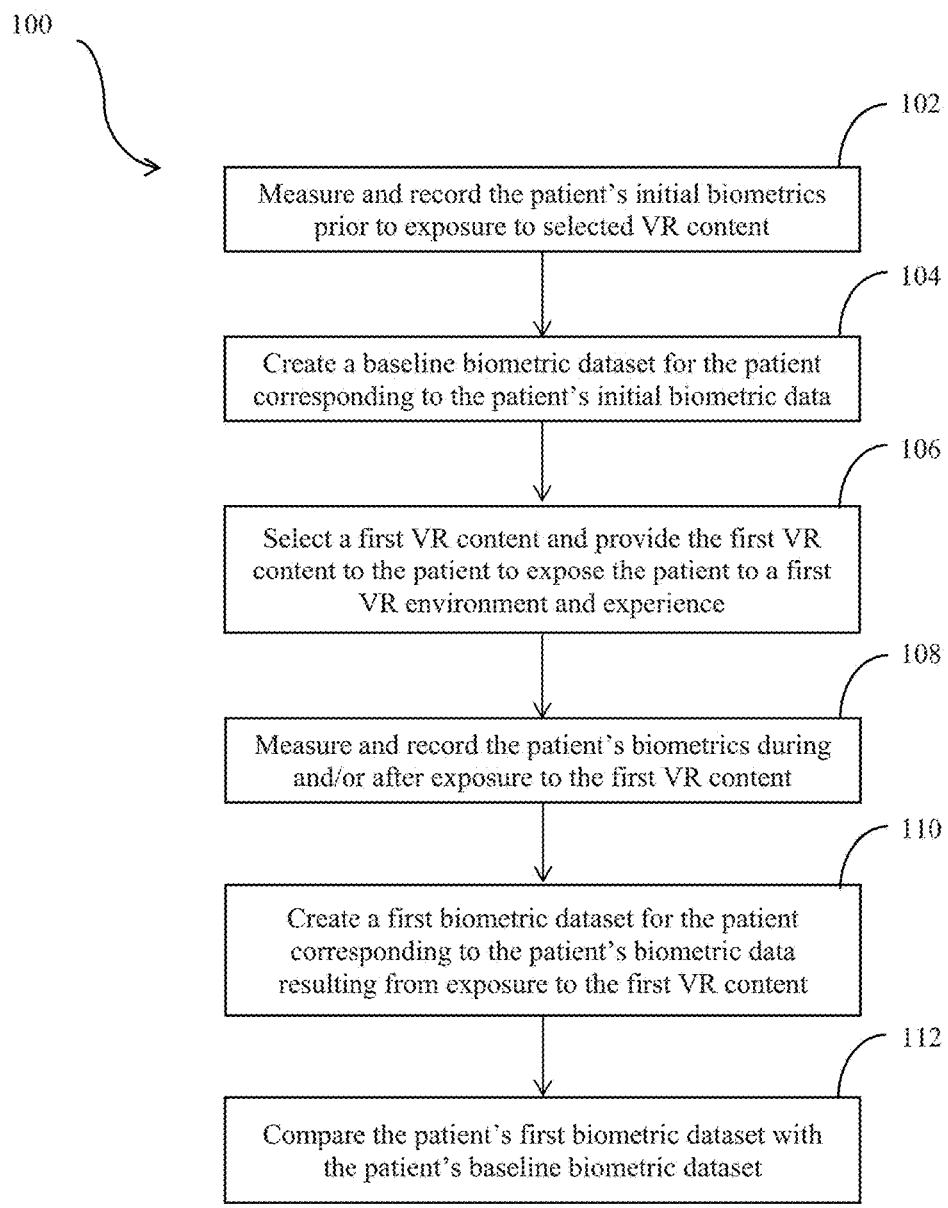
FIG. 2 is a schematic representation and flowchart of a method for utilizing virtual reality content as therapeutic treatment of psychological, psychiatric or other medical conditions in accordance with one embodiment of the present invention.

As schematically shown in FIG. 2, method 100 may begin at step 102 where the patient's initial biometrics are measured and recorded. As described above, the biometrics recorded for the patient may include EEG readings, heart rate, blood pressure, respiratory rate, and skin temperature, among others. The patient's initial biometric data recorded at step 102 can correspond to the patient's biometric readings prior to exposure to selected VR content. The initial biometric data can measured using monitoring equipment, such as biometric monitors 22-30 of system 10 described above. At step 104, a baseline biometric dataset can be created for the patient based on the initial biometric data recorded at step 102.

After creating the baseline biometric dataset, a first VR content can be selected and provided to the patient at step 106. The first VR content can be provided to the patient through a VR device, such a VR device 14 and can expose the patient to a first VR environment and experience. According to certain embodiments of the present invention, the first VR content is selected based on a selected set of criteria in order to treat a specified psychological, psychiatric or medical condition of the patient or cause desired changes in the patient's biometric associated with a specified psychological, psychiatric or medical state. The VR content can include any number of different components or features, including but not limited to visual stimuli, color, lighting, movement, camera angle, sound, music, voice, pacing, timing, characters, story arc, and script, aimed at influencing a patient's emotional, psychological and/or psychiatric state.

At step 108, the patient's biometrics may be measured and recorded in a similar manner to step 102 during and/or after exposure to the first VR content. During this step 108, depending on the particular embodiment of method 100, the patient's biometrics may be continuously measured or measured at pre-determined intervals or measured only following the completion of the first VR content. At step 110, a first biometric dataset can be created for the patient based on the biometric data measured during step 108 (and corresponding to the patient's exposure to the first VR content).

At step 112, the baseline biometric dataset and the first biometric dataset of the patient may be analyzed to determine the effect the first VR content had on the patient's biometrics associated with psychological, psychiatric or other medical conditions. According to one embodiment, at step 112, the patient's first biometric dataset is compared to the patient's baseline biometrics to determine variations in the patient's biometric data as described in greater detail below.

Figure 3:
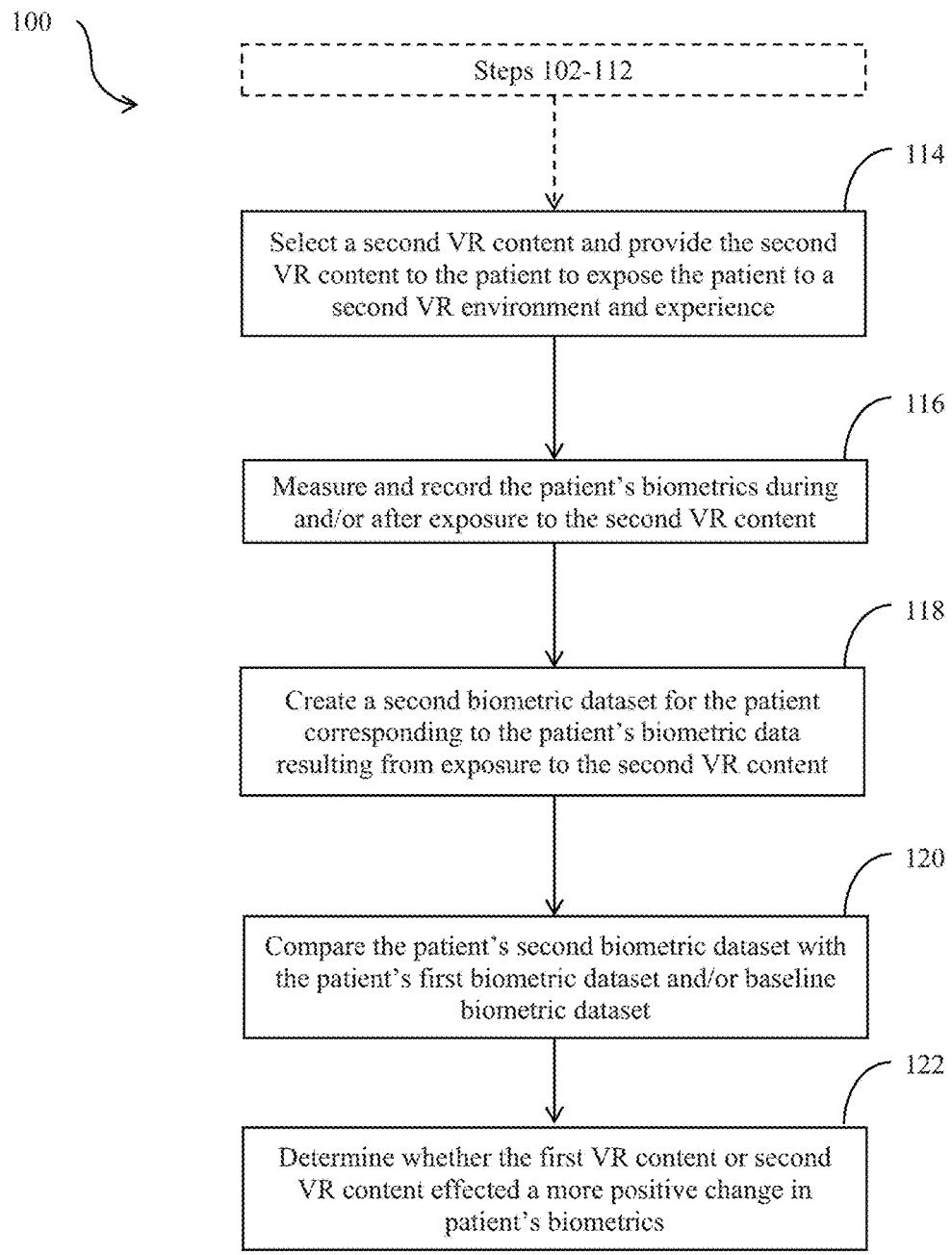
FIG. 3 is a schematic representation and flowchart of the method of a FIG. 2 including additional steps in accordance with one embodiment of the present invention.

Turning to FIG. 3, in addition to steps 102 through 112, method 100 may include additional steps in certain embodiments of the present invention. As schematically shown in FIG. 3, following step 112, according to one embodiment, method 100 may further comprise selecting and providing a second VR content to the patient to expose the patient to a second VR environment and experience at step 114. At step 116, the patient's biometrics may be measured and recorded during and/or after exposure to the second VR content in a similar manner to steps 102 and 108. At step 118, a second biometric dataset for the patient can be created based on the patient's biometric data measured during step 116. After the second biometric dataset is created, it can be analyzed and compared to the patient's first biometric dataset and/or the patient's baseline biometric dataset at step 120 to determine the effect the second VR content had on the patient's biometrics associated with psychological, psychiatric or other medical conditions.

A further shown in FIG. 3, according to one embodiment, method 100 may further comprise a step 122 where it is determined, based on the analysis at step 120, whether the second VR content effected a more positive change in the patient's biometrics as compared to the first VR content. The first and second VR contents can be varied by the visual stimuli, color, lighting, movement, camera angle, sound, music, voice, pacing, timing, characters, story arc, and script included within the particular content.

Figure 4:
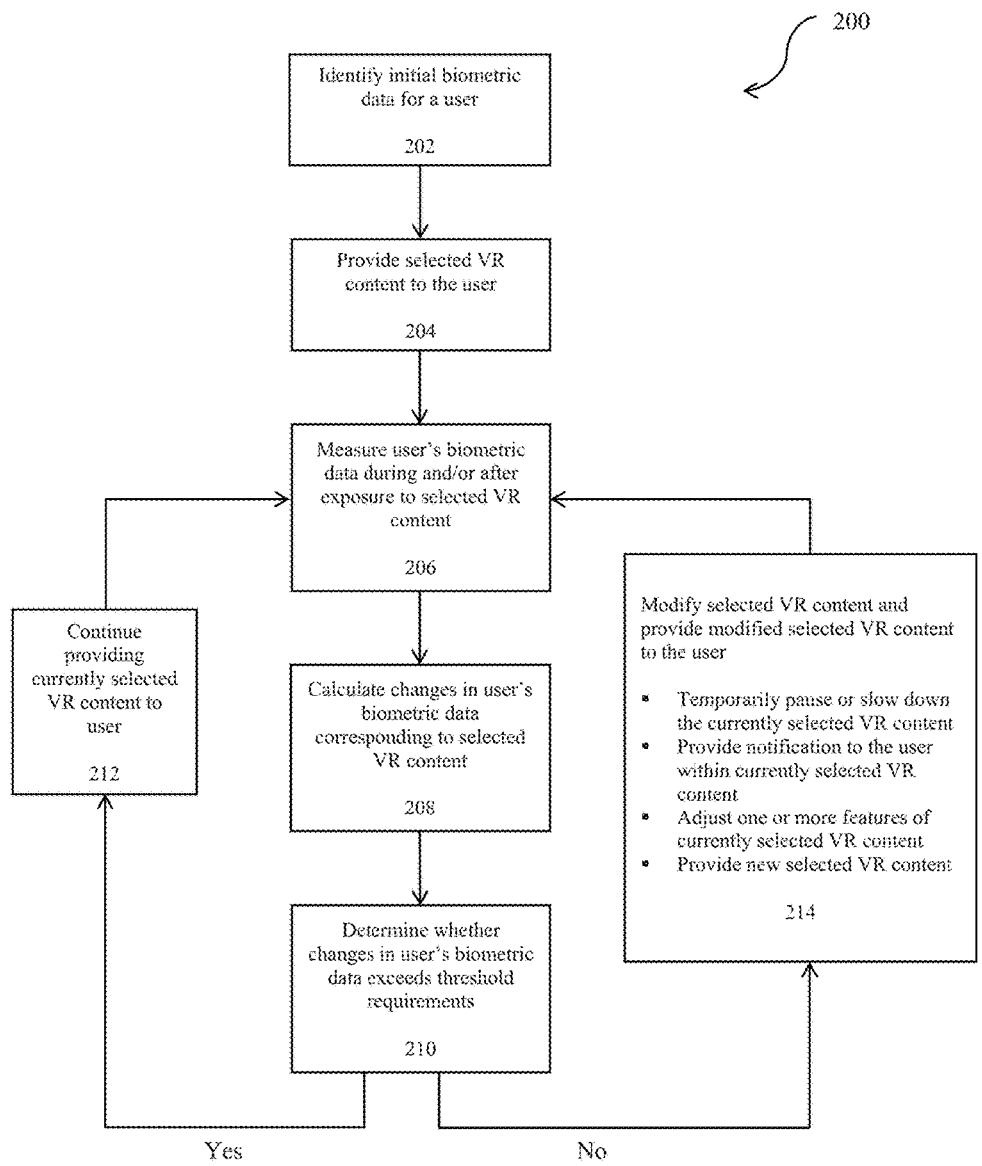
FIG. 4 is a schematic representation and flowchart of a second method for utilizing virtual reality content as therapeutic treatment of psychological, psychiatric or other medical conditions in accordance with one embodiment of the present invention.

FIG. 4 provides a schematic representation of a second method 200 according to the present invention for providing VR content to a user as therapeutic content. Method 200 can be utilized with system 10 or any other suitable system configured to provide specific VR content to a user and analyze the user's biometrics associated with the specified VR content to effect a positive change in the user's emotional, psychological and/or psychiatric state. As shown in FIG. 4, method 200 can begin at step 202 by identifying a baseline set of biometric data for a user. The baseline set of biometric data may correspond to the user's initial biometrics prior to exposure to selected VR content as measured and recorded through monitoring equipment or sensors (such as monitors 22-30 in system 10). Following step 202, a selected VR content is provided to the user at step 204 to expose the user to a selected VR experience and environment. The selected VR content may be chosen based on the specific type of emotional, psychological and/or psychiatric state to be addressed for the user. According to one embodiment, the selected VR content is chosen from a library database containing a plurality of VR content categorized based on the content's ability to influence positive change in certain types of emotional, psychological and/or psychiatric states. The selected VR content may include sound, virtual, augmented or mixed reality experiences, aroma, haptics, vestibular audio or other vibration.

As further shown in FIG. 4, at step 206, the user's biometric data is measured and recorded while the user is exposed to the selected VR content and/or after the selected VR content is completed. Depending on the particular embodiment of the present invention, the user's biometric data during step 206 may be recorded continuously or a predetermined intervals. Then at step 208, the changes in the user's biometric data is calculated by comparing the user's biometric data recorded at step 206 with the user's previously recorded biometric data and/or the user's baseline biometric dataset. The calculated changes in the user's biometric data at step 208 are designed to reflect the user's biometric reaction to the currently selected VR content as described in greater detail below.

Then at step 210, it is determined whether the changes in the user's biometric data as calculated at step 208 exceed specific threshold requirements. The specific threshold requirements may be determined based the specific type of therapeutic reaction intended to be addressed by the selected VR content and may correspond to statistically significant changes in specific biometrics of the user as illustrated in FIG. 5 and described in greater detail below.

As shown in FIG. 4, if it is determined at step 210 that the changes in the user's biometric data corresponding to the currently selected VR content exceed the threshold requirements, then the method proceeds to step 212 and the currently selected VR content continues to be provided to the user. Following step 212, the method loops back to step 206 and the user's biometric data is measured and recorded again during and/or after the selected VR content and steps 206 through 210 are repeated.

If, however, it is determined at step 210 that the changes in the user's biometric data corresponding to the currently selected VR content do not exceed the threshold requirements, the method proceeds to step 214. At step 214, a modified selected VR content is provided to the user in place of the previously selected VR content. The modified selected VR content may comprise one or more of the following modifications, depending on the particular embodiment of the present invention.

A notification may be generated and provided to the user within the currently selected VR content. The notification may be a visual or audio notification that informs the user of the current state of the selected VR content and the user's biometric data and/or provide cues or encouragement to the user.

The currently selected VR content may be temporarily paused or slowed down for a predetermined time interval and/or until specific criteria are satisfied.

One or more features of the currently selected VR content may be adjusted in order to alter the VR experience and/or environment for the user. Depending on the particular embodiment, the adjustments to the VR content may be configured to vary the visual stimuli, lighting, movement, camera angle, sound, music, voice, pacing, timing, characters, story arc, and script included within the currently selected VR content.

The currently selected VR content may be replaced with new selected VR content. The new selected VR content may comprise an entirely new or second VR content chosen from a library database containing a plurality of VR content based on the type of emotional, psychological and/or psychiatric state intended to be addressed for the user.

After providing the modified selected VR content to the user at step 214, the method may then proceed back to step 206 and the user's biometric data may be measured and recorded during and/or after exposure to the modified selected VR content and steps 206 through 210 are repeated.

One objective of method 100 and method 200 of the present invention is to provide new therapeutic methodologies implementing VR experiences, environments, and stories tailored to shift a user's brainwaves and other biometrics away from patterns associated with anxiety, depression and/or other psychological or psychiatric conditions and toward patterns associated with relaxation, positive affect, and pro-social emotional states. If subjects consistently demonstrate shifts in their biometric data toward the desired biometric data pattern (such as EEG brainwave changes, blood pressure changes, heart rate changes, etc.) and subjectively report changes in emotional or physical states consistent with the desired effect, a particular VR content experience will be identified as a targeted therapeutic intervention. For example, if a VR content experience is designed to create a relaxation response, it will be considered successful if there are biometric data shifts—such as EEG brainwave variations—indicating a reduction of activation in brain regions associated with the stress response (e.g., cingulate cortex) as well as a subjective sense of reduced stress.

If the desired brainwave patterns and/or subjective feeling state are not consistently achieved, the visual stimuli, color, pacing, voice, sound, story arc, characters, camera angle, timing, script or movement is changed in order to elicit a brain state that reflects the desired outcome. In addition, experiences can be compounded together to achieve the desired brain pattern as provided in the steps of methods 100 and 200 described above.

As also described above, the biometrics measured in connection with methods 100 and 200 of the present invention may include EEG (brainwave activity), blood pressure, skin temperature, skin conductance, respiration rate, and heart rate variability. In order to identify positive changes in a user's biometric data corresponding to exposure to certain VR content, the user's biometric data measured before, during and/or after the user is exposed to the VR content may be analyzed. As provided at steps 112 and 120 in method 100 and steps 208 and 210 in method 200 described above, the user's biometric data may be analyzed by comparing biometric data measured during and/or after exposure to VR content with biometric data measured before exposure to the VR content to identify changes in specific types of biometric data. As further provided in method 200 at steps 212-214, when it is determined by analyzing the user's biometric data that the VR content is not providing the desired changes in the user's biometric data, the VR content can be modified or altered to provide a more suitable VR content. Similarly, method 100 with reference to steps 112 and 120, may further include one or more of: (i) comparing EEG biometric data (i.e., brainwave patterns) in the first set of data with brainwave patterns in the baseline set of data (or the second set of data with the first set of data), wherein the brainwave patterns may include beta, alpha, theta, and delta brainwave patterns, (ii) analyzing the location within the patient's brain in which the brainwave patterns of the first set of data or the second set of data occur, and (iii) continually or periodically modifying the patient's brainwave activity by exposing the patient to additional instances of the first environment.

According to one embodiment of the present invention, the analysis of a user's EEG-type biometric data may be analyzed as quantitative EEG (Qeeg) data using brainwave analysis software, such as but not limited to brainwave analysis software provided by BrainAvatar®. According to one embodiment, the EEG biometric data of the user may be measured during and/or after exposure to the VR content and compared to previously measured EEG biometric data of the user to produce z-scores of change for specific brainwave types (alpha, delta, theta, etc.) in certain regions of the brain. This process may be facilitated by using sLORETA statistical procedures. The creation of z-scores for the various Qeeg types of brainwave data (i.e., alpha, delta, theta, etc.) can then be used to quantitatively identify meaningful changes in the user's EEG biometric data. For example, z-score changes equal to or greater than 1.0 z-score/standard deviation may be classified as statistically significant. Other types of biometric data, such as respiratory rate, heart rate, blood pressure, etc., may be analyzed in a similar manner to identify statistically significant z-score changes in a user's biometric data resulting from exposure to selected VR content.

According to one embodiment, the z-score changes identified in the user's biometric data as a result of exposure to selected VR content may be used to determine whether the selected VR content is having a positive effect on the user's emotional, psychological or psychiatric state. Changes in specific types of biometric data have been shown to enact changes is specific types of emotional, psychological or psychiatric states of subjects. For example, increased levels of delta, theta, and alpha EEG brainwaves generally are linked to a more calm and relaxed state of a patient. Similarly, decreased blood pressure, heart rate and respiratory rate levels are also linked to a more calm and relaxed state. Accordingly, when the desired effect of the selected VR content is to place the user in a relaxed or stress-reduced state, the systems and methods of the present invention may be configured to identify statistically significant z-score changes indicating increases in a user's delta, theta and alpha EEG level along with significant reductions in blood pressure, heart rate and respiratory rate biometric data levels. When these significant changes are identified during exposure to selected VR content, then that VR content is providing a therapeutic response to enact a positive change in the user's emotional, psychological or psychiatric state.

The analysis of a user's biometric data as described above may also be used to create specific threshold requirements for identifying whether a particular VR content is enacting the desired effect on the user's emotional, psychological or psychiatric state and determining whether changes in a user's biometric data exceed such threshold requirements as utilized in method 200. The threshold requirements utilized at step 210 of method 200 may be determined based on the desired emotional, psychological or psychiatric response for the user. A selected VR content can be specifically configured to cause changes in a user's biometric data associated with relaxation, focus, empathy, calmness, mindfulness. These various types of reactions have been shown to cause changes in a user's emotional, psychological or psychiatric state, and therefore the VR content provided to the user through method 100 or 200 of the present invention, and the analysis of the user's change in biometric data resulting from the VR content can be categorized based on the desired types of reactions of the user to the VR content.

For example, FIG. 5 illustrates five different types of neuromeditation styles profiles in accordance with the present invention that may be utilized in connection with methods 100 and 200. These neuromeditation styles may include stress reduction/pain reduction 300; mindfulness 302; focus 304; open hear 306 and quiet mind 306. These neuromeditation styles may be used to categorize VR content so that particular VR content may be selected based on the therapeutic preferences for the user in connection with methods 100 and 200 of the present invention. As also further shown in FIG. 5, the threshold requirements at step 210 in method 200 may be determined based on the particular neuromeditation style of the VR content determine whether the desired changes in emotional, psychological or psychiatric states of the user are being achieved.

Exemplary Case Studies

Applications of the present invention in accordance with methods 100 and 200 describe above and illustrated in FIGS. 2-4, and other various aspects will now be described with respect to three case study summaries.

Case Study #1—Virtual Reality Meditation: Changes in Brainwave Activity and Heart Rate Variability Popular articles that discuss brainwaves in relation to states of consciousness often simplify matters by indicating that there are four types of brainwaves: delta, theta, alpha, and beta. Delta, theta, and alpha can all be considered "slow" brainwaves. When they are dominant, the brain is often in a more relaxed or quiet state. Beta and brainwaves faster than beta, such as high beta or gamma, can be considered "fast" brainwaves. When these are dominant, the brain is active and engaged. We need these brainwaves to be flexible and fluid, shifting and changing with whatever task we give our brain. For example, when it is time to rest, we expect slow brainwaves to increase and fast brainwaves to decrease. When we are balancing a checkbook or making an important decision, we expect the opposite pattern.

By measuring brainwaves (i.e., biometric data) before and after a specific task or experience, it can be determined how the brain was impacted. In doing so, analysis can assist in determining whether the brain became more alert and aroused or more relaxed and quiet.

In order to determine how the brain responds when someone engages in a virtual reality meditation, quantitative EEG biometric data (Qeeg) technology can be utilized.

In the first case study, a volunteer subject was first oriented to virtual reality by having them watch two different StoryUP™ immersive stories. After the orientation, a baseline measurement of their brainwaves (i.e., biometric data) using a 19 channel EEG system was obtained. The volunteer subject then participated in a four-minute mindfulness in nature experience (i.e., a selected VR content), after which the brainwaves (i.e., biometric data) were one more time.

Overall, the results showed a significant quieting of the brain after experiencing the brief VR content meditation, measured by decreases in fast activity (gamma) and increases in slow activity (theta and alpha). This, by itself, was impressive given the relatively brief exposure to the meditation. Perhaps more importantly, an analysis of specific brain regions impacted by the VR content meditation showed that areas of the brain involved in the stress response were some of the most significantly impacted.

Figure 6A:
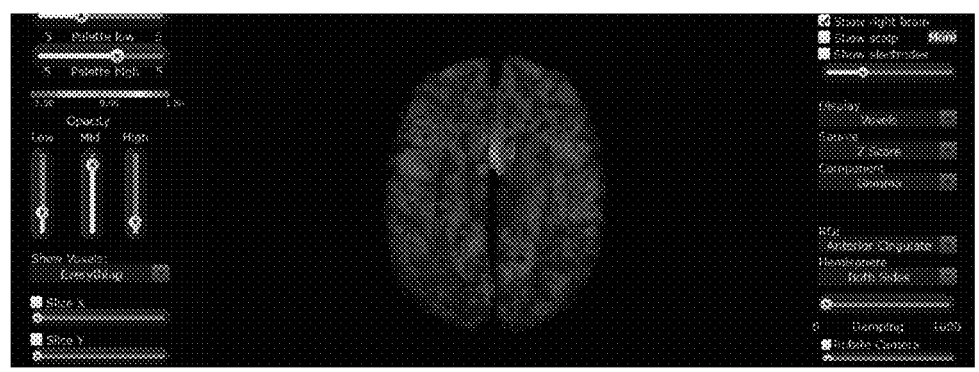
FIG. 6A is a brain image taken during a first case study.
Figure 6B:
FIG. 6B is a brain image taken during a first case study.

Three-dimensional brain images showing changes in the brain of the volunteer subject after the exposure to the VR content were generated. For reference, cooler colors (blues) indicate that the activity measured has decreased whereas brighter colors (yellow, orange, red) indicate that activity has increased. FIG. 6A illustrates fast brainwave activity (e.g., gamma) in the anterior cingulate. Blue colors indicate that fast brainwave activity decreased significantly during the meditation. FIG. 6B illustrates slow brainwave activity (e.g., alpha) in the Precuneus region of the brain. Yellow colors indicate that slow brainwave activity increased during the meditation.

Fast brainwave activity (e.g., gamma) in the anterior cingulate was identified by the appearance of blue colors indicating that gamma activity decreased significantly during the VR content meditation. This is important because this part of the brain often becomes over activated during stress and anxiety or when a subject becomes fixated on thoughts, feelings or behaviors. By helping this area to relax, the brain is shifting into a more relaxed, peaceful state.

Slow brainwave activity was the subsequently examined for the volunteer subject. In particular, specific identification of alpha brainwave activity in the Precuneus region of the brain was examined. Additional examination showed increased slow brainwave activity (e.g., alpha) in the Precuneus region of the brain. This part of the brain is the hub of the brain's Default Mode Network (DMN). When the DMN is quieter, as occurred here, this suggests that the subject is not thinking about themselves (or their worries) as much, which is exactly what we would hope to see during this experience.

These results of this case study provide preliminary evidence that this type of technology can have a nearly immediate impact on the stress response.

Case Study #2—The Impact of Virtual Reality Mindfulness Meditation on the Brain

In the second case study, the subject was a 16-year-old male with a history of anxiety following a mild traumatic brain injury. Prior to beginning the study, the subject was oriented to virtual reality by watching a three-minute VR news story.

EEG biometric data was recorded in 19 channels using an EEG monitoring device, as in case study #1, before, during, and after the subject watched a five-minute mindfulness in nature VR experience (i.e., selected VR content) created by StoryUP™ VR.

Figure 7A:
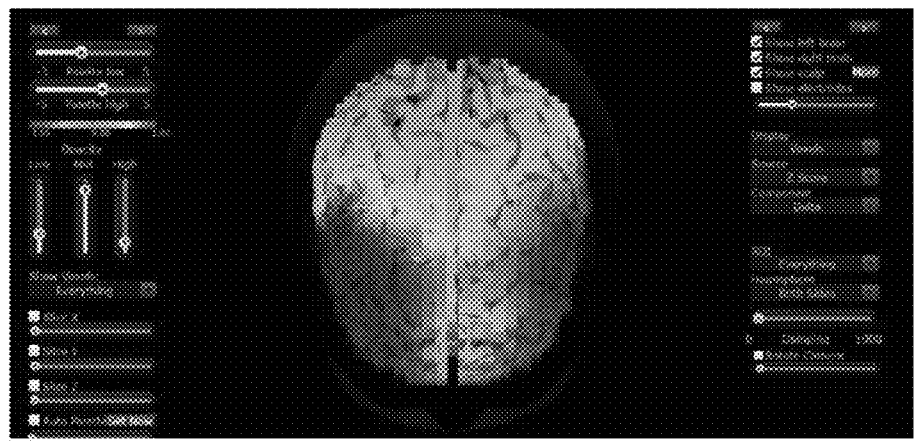
FIG. 7A is a brain image taken during a second case study.
Figure 7B:
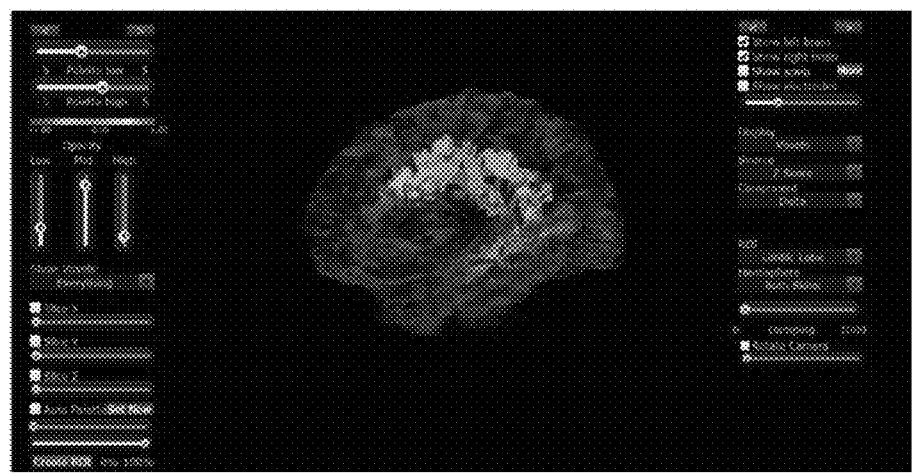
FIG. 7B is a brain image taken during a second case study.

When comparing the EEG biometric data during the experience to the baseline biometric data, the largest changes were observed in delta brainwaves (1-4 hz). Delta is a cluster of the slowest brainwaves. Increases in delta are generally accompanied by a decrease of conscious thought or, put another way, a "quieting of the mind." Several changes in the subject's EEG biometric data occurred during the VR content meditation in the delta frequency range. Most of the changes were in the front and sides of the brain. FIG. 7A illustrates a quieting of the frontal regions, which suggests a lack of cognitive processing. Diving a bit deeper into the brain, the limbic structure was significantly involved in this quieting response, as demonstrated in FIG. 7B. This is potentially important as the limbic system is involved in emotional processing.

Figure 7C:
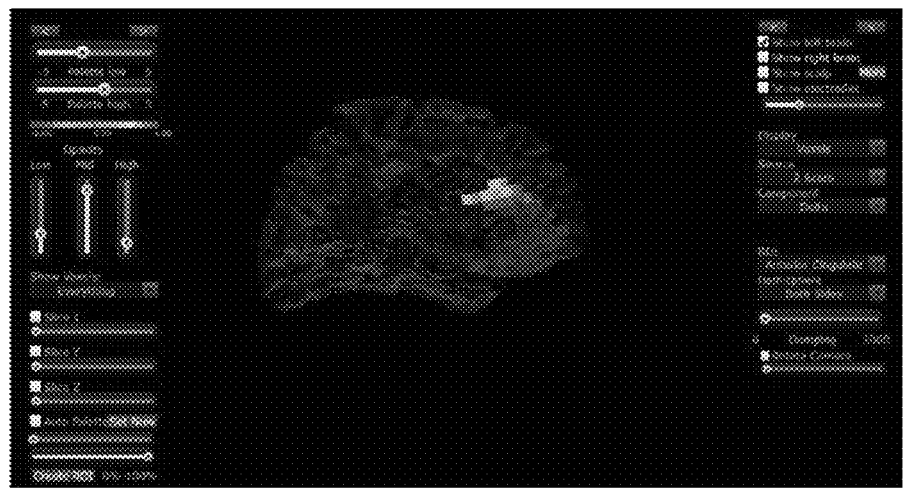
FIG. 7C is a brain image taken during a second case study.
Figure 7D:
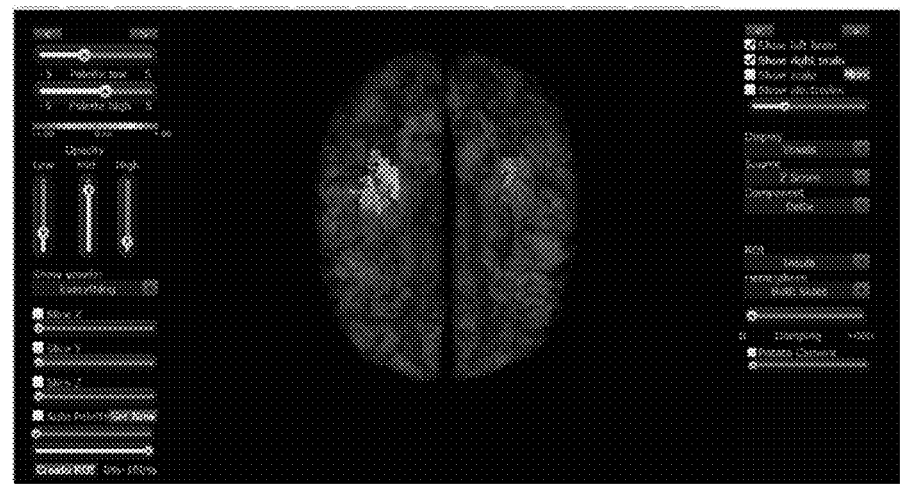
FIG. 7D is a brain image taken during a second case study.

Examining even more specific structures, the anterior cingulate and the insula both showed dramatic increases in delta activity, as illustrated in FIGS. 7C and 7D. The anterior cingulate is involved in focusing attention and emotion regulation. The *insulae* are involved in body awareness and emotional responses. The quieting of these regions suggests that this subject experienced a significant relaxation of these regions which are often over-activated during anxiety or a stress response.

This is the second case study demonstrating reduced brain activation in response to experiencing a VR-based mindfulness meditation (i.e., selected VR content). These results suggest that this technology may be a useful adjunct to traditional treatments for anxiety and/or stress-related concerns.

Case Study #3—Can Virtual Reality be Used to Develop Empathy and Compassion?

In the third case study, the subject was a 68-year-old female. EEG biometric data was recorded in 19 channels, as in the prior case studies, before and after the subject watched a five-minute story about a group of individuals in Zambia that did not have the use of their legs (i.e., selected VR content). In the story, these individuals are presented with hand crank Personal Energy Transportation (PET) carts, allowing them mobility they have not experienced in many years. The story was created by StoryUP™ VR and is designed to increase empathy and compassion in the viewer. After completing the EEG biometric data recordings, the subject was asked to write a few statements about what she was feeling or thinking after the experience. The subject wrote the following list:

Sadness
Hope
Despair
Gratitude
Sympathy
Wanting to help
Sense of community

When comparing the EEG data after the experience to the baseline data, the largest changes were observed in gamma brainwaves (35-45 hz). Gamma represents the fastest brainwaves and is associated with increased cognitive processing as well as a synthesizing of information.

With respect to the changes in biometric data that occurred after the VR content story, bright colors (yellow, orange, red) were present indicating a significant increase of gamma activity after the VR content experience. After watching the VR story, this subject demonstrated significant increases of gamma activity in the left hemisphere of the brain.

As demonstrated in FIG. 8A, these increases were seen predominately in the parieto-occipital area toward the back of the head and also along the sensory motor strip. It is possible that this reflects a combination of visual and body oriented processing. Because it is on the left hemisphere, this subject was likely engaging in some kind of language-oriented processing, perhaps attempting to integrate and make sense out of what was just experienced.

In an attempt to understand these findings in more detail, the analysis was extended using sLORETA analyses to examine changes in deeper structures of the brain. This analysis revealed significant increased gamma activation in the Lingual Gyms.

As demonstrated in FIG. 8B, the changes identified in the Lingual Gyms support the notion that there was some level of language processing involved. It is likely that the subject was engaged in some level of internal "talk," while processing the story.

Figure 8C:
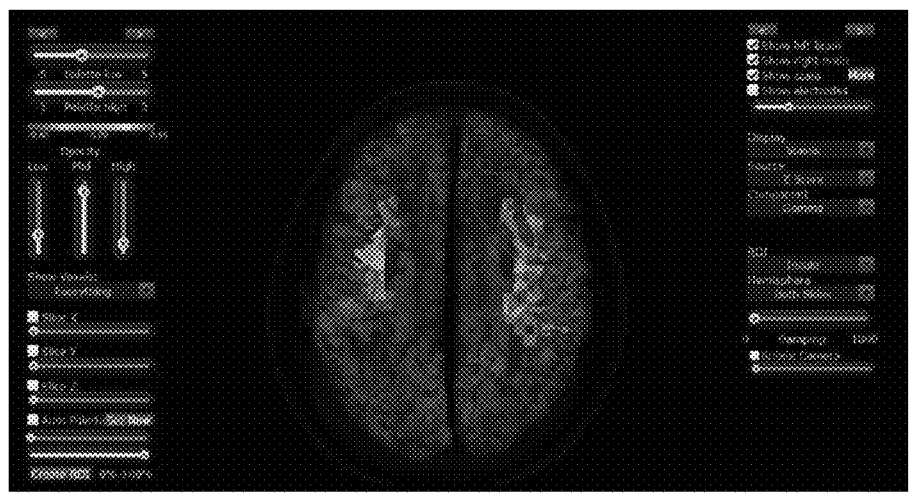
FIG. 8C is a brain image taken during a third case study.

As shown in FIG. 8C, an increased activation in the posterior portion of the left Insula was also identified. The Insula is important in emotional processing, empathy and the experience of internal bodily states (e.g., heart beat). This activation is consistent with the subject reporting the experience of a number of emotional states including empathy, sadness, and hope.

Figure 8D:
FIG. 8D is a brain image taken during a third case study.

As shown in FIG. 8D, an activation of the left Parahippocampal Gyms was also identified. This region of the brain is generally associated with memory encoding or retrieval. This activation is likely to be the result of the subject attempting to integrate her experience with what she knows and understands from previous experiences and knowledge.

The results of this case study show that a brief VR content experience can induce both subjective feelings of empathy and compassion, and also activate regions of the brain important in the processing of these complex emotional states. These preliminary results provide additional evidence that selected VR content can be used to assist in the development of prosocial emotional states.

The methodology for this therapeutic use of virtual reality differs from prior art in that it is manipulating experiences or stories to achieve specific biometric data change patterns (such as specific changes in brainwave patterns, heart rate, respiratory rate, blood pressure, etc.). In pre-existing applications, the effects of these treatments are not categorized by biometric states. The prior art also does not specify how to change the biometric patterns or brainwave patterns by changing voice, music, visual stimuli, pacing, script, camera angle, or camera movement.

VR Content Categorization

The present invention is also directed toward methods and applications for structuring, categorizing and providing selected VR content in connection with methods 100 and 200 of the present invention. Therapeutic VR content may be tagged by its ability to create percentage shifts in the amplitude of specific biometric data (e.g., brainwave frequencies). Much as a video is tagged by a keyword that's searchable, the immersive media experiences of the selected VR content may be tagged by keywords related to the emotion, state of consciousness, or biometric or brainwave activity they produce in a statistically significant number of individuals. This content may include sound, virtual, augmented or mixed reality experiences, aroma, haptics, vestibular audio, or other vibration. As described above, specific VR content experiences have been shown to result in predictable changes in biometric and brainwave patterns. As also described above, this may be assessed by comparing pre-VR biometric data to post-VR biometric data.

For example, with respect to EEG biometric data, EEG (Qeeg) data may be analyzed using BrainAvatar® analysis software or other similar software. The BrainAvatar® system has a feature called Z-builder which allows for the conversion of a raw EEG file into a quantitative reference file. Post-VR (or During-VR) EEG data can be compared to the Pre-VR reference file producing z scores of change for each variable at each region of interest for each subject. The brain wave values can be produced through the BrainAvatar® software, which calculates the average amount of power for each frequency band (e.g., delta, theta, alpha, etc.) at multiple regions of interest using sLORETA statistical procedures. Based on recognized research, z score changes equal to or greater than 1.0 z-score/standard deviation are considered statistically significant. Consequently, VR content experiences can be created based on the ability to consistently demonstrate significant changes in the biometric data of a subject in a variety of specific ways, such as those illustrated in FIG. 5.

According to one embodiment of the present invention, a database of VR content (such as VR content database module 16 in system 10) may be created and the VR content therein may be categorized by the content's impact of specific biometrics much like a pharmacy. Specific VR content can be constructed to consistently increase alpha (relaxation), reduce beta (anxiety), or increase left frontal gamma (Positivity), reduce blood pressure, increase respiration, increase peripheral skin temperature, decrease skin conductance, and slow the heart rate. Using a brain-computer interface, heart rate, respiration or blood pressure monitor (such as monitors 22-30 in system 10), a user's biometrics can be assessed for patterns associated with specific concerns (anxiety, depression, pain, etc.). Based on these results, the user may be offered a selection of experiences specifically designed to address areas of concern/biometric patterns. For example, users demonstrating the certain types of profiles (such as stress reduction/pain reduction 300, mindfulness 302, focus 304, quiet mind 306 and open heart 308) will be recommended the VR content specific to such profiles.

According to one embodiment of the present invention, a user may begin by taking a questionnaire and/or symptom checklist configured to determine the user's specific goals/needs (such as stress reduction, improving focus, etc.) and identify the specific type of profile best suited for the user. This questionnaire and checklist may comprise the NMSI or neuromeditation style inventory questionnaire/symptom checklist provided by NeuroMeditation™ or any other suitably configured questionnaire. With respect to methods 100 and 200 of the present invention, this process may be provided as an initial step conducted prior to steps 102 or 202, respectively. The questionnaire may be answered by the user inside a VR headset with gaze direction or outside a VR headset with another device such as a mobile phone or tablet.

Depending on the user's responses to the questionnaire and/or symptom checklist, the user may be presented with a library of VR content designed to address the user's specific goals/needs. The VR content may also be categorized by specific neuromeditation style or profile (Focus, Mindfulness, Open Heart, Quiet Mind, Deep States). The VR content experiences may be passive "viewer" experiences and/or they may include inputs from biometric monitoring devices to interact with the experience like heart rate, blood pressure, or respiration.

According to one embodiment of the present invention, certain VR content may be utilized with biometric devices (such as monitors 22-30 in system 10) to import specific information about the user's biometrics inside the VR content experience. As described above, specific biometrics may include EEG (brainwave data), blood pressure, skin temperature, skin conductance, respiration rate, and heart rate variability. The user is able to see a representation of their biometrics in the experience singularly or collectively. Using an algorithm, a single or combination of biometric outputs may be assigned to values in the virtual reality environment of the selected VR content to enable the user to control the experience with their biometric activity, such as their brainwave activity, blood pressure, heartrate variability, skin conductance, skin temperature, respiration, or some combination of these measurements. The biometric outputs can be set to modify the VR Content's experience's volume, light, color, tone, depth, aroma, sound, pitch, or texture. In addition, these biometrics may be utilized to control a 360 video player by allowing pre-defined biometric values to stop, start, pan, tilt, zoom, slow, or speed up a monoscopic or stereoscopic video or audio clip.

As described above, depending on the user's responses to the questionnaire/symptom checklist, the user is able to select a specific VR content from a library of immersive VR content experiences that have been shown to consistently impact specified biometrics, anxiety level, focus, open heart, open mind, blood pressure, respiration, heart rate or perception of pain, along with any number of other emotional, psychological and/or psychiatric states.

According to one embodiment of the present invention, after consuming the selected VR content experience, a display of biometric changes may be displayed to the user, indicating to the user the impact of the selected VR content experience on the targeted biometric readings. Depending on the particular embodiment, this may comprise an additional step within methods 100 and 200 described above. For example, brain activity measurement obtained through a brain computer interface (BCI), such as the Muse, Neurable, or Emotiv, can monitor specific aspects of brainwave activity during the experience and display whether the content intervention was effective in changing the targeted brain region(s). Similarly, a blood pressure, heart rate, skin temperature, skin conductance, respiration and/or other biometric monitor may be used to determine whether the content was effective in its intended effect. The user may also be able to retake the symptom inventory to determine if there has been any change in their subjective feeling state. Based on the results of the subjective questionnaires and/or biometric data analysis, additional VR content options may be offered to further achieve the desired effect. If the VR content intervention was effective, the user may also choose to end the experience, continue to view additional VR content or start the process again.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

The invention claimed is:

1. A method for using virtual reality or augmented reality experiences as therapeutic treatment to improve the emotional, psychological, or psychiatric state of a user, said method comprising the steps of:

identifying initial biometric data for the user, wherein said initial biometric data includes EEG brainwave activity of the user, wherein said EEG brainwave activity includes at least one of beta, alpha, gamma, theta, and delta brainwave activity;

selecting virtual reality content for the user based at least in part on the emotional, psychological, or psychiatric state desired to be improved; wherein said selected virtual reality content comprises at least one of a virtual reality environment, an augmented reality environment and a mixed reality environment;

providing the selected virtual reality content to the user;

measuring the user's biometric data during and/or after the user's exposure to the selected virtual reality content; wherein said measured biometric data includes EEG brainwave activity of the user during and/or after the user's exposure to the selected virtual reality content, wherein said EEG brainwave activity includes at least one of beta, alpha, gamma, theta, and delta brainwave activity;

calculating changes in the user's biometric data corresponding to the selected virtual reality content, wherein the calculation of changes includes calculating changes in at least one of the user's beta, alpha, gamma, theta, and delta brainwave activity;

determining whether the calculated changes in the user's biometric data exceed a set of threshold requirements, wherein at least one threshold requirement of said set of threshold requirements includes an increase in at least one of the user's beta, alpha, gamma, theta, and delta brainwave activity;

continuing to provide the selected virtual reality content to the user if the calculated changes in the user's biometric data exceed the set of threshold requirements; and modifying the selected virtual reality content and providing the modified selected virtual reality content to the user if the calculated changes in the user's biometric data do not exceed the set of threshold requirements.

2. The method of claim 1, wherein the step of modifying the selected virtual reality content includes at least one of temporarily pausing or slowing down the selected virtual reality content, providing a notification to the user through the selected virtual reality content, adjusting one or more features of the selected virtual reality content and providing a new selected virtual reality content.

3. The method of claim 1, wherein the step of calculating changes in the user's biometric data includes comparing the EEG brainwave activity of the initial biometric data with the EEG brainwave activity of the measured biometric data.

4. The method of claim 3, wherein the step of calculating changes in the user's biometric data further includes creating one or more z-scores corresponding to changes in the EEG brainwave activity of the user.

5. The method of claim 4, wherein the calculated changes in the user's biometric data exceed the set of threshold requirements includes when at least one of said one or more z-scores has a value greater than or equal to 1.0.

6. The method of claim 1, wherein the step of modifying the selected virtual reality content includes changing at least one of the visual stimuli, color, lighting, movement, camera angle, sound, music, voice, pacing, timing, characters, story arc, and script of the selected virtual reality content.

* * * * *